United States Patent [19]

Imre et al.

[11] 3,996,294
[45] Dec. 7, 1976

[54] OXIDIZING METHANE TO FORMALDEHYDE

[75] Inventors: Laszlo Imre, Cologne; Heinrich Nassenstein, Leverkusen-Steinbuechel, both of Germany

[73] Assignee: Bayer Aktiengesellschaft, Leverkusen, Germany

[22] Filed: Jan. 23, 1975

[21] Appl. No.: 543,700

[30] Foreign Application Priority Data

Feb. 1, 1974 Germany .......................... 2404737

[52] U.S. Cl. .................................. 260/604 R
[51] Int. Cl.² .................................. C07C 45/02
[58] Field of Search ........................ 260/604 R

[56] References Cited

UNITED STATES PATENTS

| | | | |
|---|---|---|---|
| 2,244,210 | 6/1941 | Nashan | 260/604 R |
| 2,467,993 | 4/1949 | Rossman | 260/604 R |
| 3,027,411 | 3/1962 | Murphy | 260/604 R |
| 3,761,424 | 9/1973 | Koberstein et al. | 260/604 R |

*Primary Examiner*—James O. Thomas, Jr.
*Assistant Examiner*—W. B. Lone
*Attorney, Agent, or Firm*—Burgess, Dinklage & Sprung

[57] ABSTRACT

In the gas phase reaction of methane and oxygen at elevated temperature to form formaldehyde, the improvement which comprises effecting the reaction in the presence of silicon dioxide as catalyst, the silicon dioxide having a large internal surface area. Other metal oxides may be mixed with the silicon dioxide.

4 Claims, No Drawings

OXIDIZING METHANE TO FORMALDEHYDE

The present invention concerns a method of preparing formaldehyde by oxidizing methane with oxygen.

A number of processes have become known for the preparation of formaldehyde by the partial oxidation of methane. One of these processes sets out from natural gas (98% methane), which is racted with air in the presence of nitrogen oxides as catalyst at 600° C (cf. F.I.A.T. Final Report No. 1085; Ullmann, Encyklopadie der Technischen Chemie, 3rd ed., vol. 7, pp. 663–665 (1956)). In this process a selectivity of 9.7% (percent of moles of reacted methane which are converted to formaldehyde) and formaldehyde yields of 130 g per $Nm^3$ of methane are achieved. Methanol, formic acid, carbon monoxide and carbon dioxide are produced as by-products.

In a modification of this process, solid catalysts are used in addition to the nitrogen oxides (cf. Ullmann, loc. cit., and Austrian Pat. Nos. 136,669, 156,069 and 158,644), selectivities of 1.7 to 21.3% and formaldehyde yields of 23 to 285 g per $Nm^3$ of methane being obtained. 0.13 to 3.5 kg of nitrogen oxide is consumed for the production of 1 kg of formaldehyde.

In another modification of this process (cf. German Pat. No. 1,050,752), in addition to nitrogen monoxide, a catalyst located in a fluidized bed is used, which has good heat transfer characteristics. The gases leaving the reaction chamber are cooled by a second fluidized bed. By this method formaldehyde can be obtained generally in selectivities of the kind achieved in the processes described further above. The reaction temperature in this process amounts to 470° C, and therefore only low volumetime yields can be attained, which are technically unattractive. This process is difficult to manage on account of the complicated nature of the apparatus used.

A process has also been described in which methane is reacted with oxygen in the presence of nitrogen oxides in what is termed an "inverted flame," with the formation of formaldehyde (cf. German published specification DAS No. 1,217,353). In this process, 40 grams of formaldehyde can be obtained per $Nm^3$ of methane input. Another method uses vaporous nitric acid as catalyst instead of nitrogen oxides (cf. German published specificiation DAS No. 1,159,421).

All these processes have the disadvantage that the gaseous catalyst has to be fed to the starting products continuously, sometimes in very great quantities. The gas mixtures which are obtained, containing nitrogen oxides or nitric acid vapors, are very corrosive, and as a result all parts of the apparatus must be made of high-grade material. The formaldehyde formed by these processes always contains nitric acids as impurities, which are very difficult to remove and have a corrosive action. Furthermore, the preparation of ammonia, nitrogen oxides or nitric acid involves additional expense.

Other processes have become known in which oxygen, sulfur dioxide or sulfur dioxide enriched with ozone are used as oxidants for the preparation of formaldehyde from methane (cf. Ullmann, supra; J. F. Walker Formaldehyde, 3rd ed., New York (1964), pp. 25 to 27, and U.S. Pat. Nos. 2,532,930 and 2,590,124). As it is stated in the first two works, these processes have nevertheless not gained acceptance in the art.

Finally, in German published specification DOS No. 2,201,429, the gas phase oxidation of methane with air in a reaction zone in the form of a flame is described. The average residence time in the flame zone must be kept within close limits, which is very difficult to accomplish. In this process, formaldehyde can be obtained in quantities of up to about 300 g per $Nm^3$ of methane input. In addition, considerable amounts of methanol are produced.

It is accordingly an object of the present invention to provide a simple process for oxidizing methane to formaldehyde.

This and other objects and advantages are realized in accordance with the present invention pursuant to which methane and oxygen are reacted in the gas phase at elevated temperature to form formaldehyde, the reaction being effected in the presence of silicon dioxide as catalyst, the silicon dioxide having a large internal surface area.

The catalysts to be used in accordance with the invention can consist exclusively of silicon dioxides. However, mixtures of silicon dioxide with other oxides can also be used, e.g., with oxides of aluminum, iron, vanadium, molybdenum, tungsten, calcium, magnesium, sodium or potassium. Such mixtures can contain up to about 50% by weight of such other oxides, preferably at least about 5% when present. The proportions of such other oxides can, for example, be the following: up to about 10% each of $Al_2O_3$, CaO and/or MgO, and up to about 5% each of $Na_2O$, $K_2O$ and/or iron oxides. Such catalysts can also contain traces of sodium chloride. The catalysts to be used in accordance with the invention can contain up to about 2% water by weight.

For example, the silicic acid products prepared by the method described in German published specification DOS No. 1,767,754 are suitable as catalysts for the process of the invention. In accordance with that specification, porous, attrition-resistant, pearl-like products containing mostly silicic acid are obtained by: suspending in an aqueous, stable silicic acid sol having a specific surface area of 150 to 400 $m^2/g$ BET (Brunauer, Emmet and Teller, Journal of the American Chemical Society, 60, p. 309 (1938)) a siliceous filler having a specific surface area of 20 to 200 $m^2/g$ BET in amounts of 20 to 60 wt. % (with respect to the dry granular product) and clay minerals of the kaolinite, montmorilonite and attapulgite group in amounts of 5 to 30 wt. %; mixing this suspension with an aqueous suspension of hydrated finely divided oxide in amounts of 0.1 to 3 wt. % (with respect to the anhydrous granular product); dividing this gelable mixture into drops of the desired size; causing the drops to gel in a liquid that is not miscible with water, thereby forming a pearl-like granular product; separating the granules from the liquid; the granules then being dried and then hardened for at least ten minutes at temperatures of 500° to 1000° C. At a constant exposure to about 750° C, the chemical and physical properties of these silicic acid products remain unaltered (cf. also L. Dorn, G. Heinze and E. Podschus, Erdol und Kohle, 23, pp. 648 to 651 (1970)).

For the process of the invention, catalysts are generally used which have an internal surface area of more than about 30 $m^2/g$ BET. For example, catalysts having an internal surface area of about 50 to 500 $m^2/g$ BET or about 80 to 250 $m^2/g$ BET can be used.

The catalyst may be in different forms, for example, in powder form, in coarsely granular form, spherical, sausage-shaped, tablets or cylindrical bodies and it may be used in a fixed bed or, for the better elimination of heat, in a fluidized bed or in any other kind of agitated catalyst bed. In fluidized bed operation, spherical catalyst particles of a diameter of about 0.01 to 2 mm, for example, are suitable. In the fixed bed, catalyst particles of any desired shape and having a particle size of generally about 0.2 to 20 mm can be used. For example, sausage-shaped particles with a length of about 4 to 18 mm, or balls of a diameter of about 0.4 to 10 mm are suitable.

Especially to be preferred is a pure silicon dioxide catalyst characterized as follows: internal surface area about 80 to 250 m$^2$/g BET, spherical particles of a diameter of about 0.4 to 4 mm, disposed in a fixed bed or fluidized bed.

If the catalyst's activity should be reduced by the deposition of carbon, its original activity can easily be restored by burning it off in the presence of air at elevated temperature, such as for example 400° to 750° C.

The process of the invention is performed in the gas phase. Pressure, temperature, composition of the starting products and rates of flow may vary widely within the limits of gas phase operation.

The process of the invention can be performed at normal pressure, reduced pressure, or elevated pressure. Suitable pressures are, for example, 1 to 100 atmospheres. Preferably the process is performed at pressures from about normal to 30 atmospheres. Generally, the reaction temperatures range between about 450° and 750 C. The process can be performed, for example, at temperatures from about 500° to 700° C, preferably at about 520° to 670° C.

The starting products, methane and oxygen, can be used in pure form or mixed with other gases. For example, methane can be used in mixtures with other hydrocarbons, such as ethane, propane, butane, pentane, hexane, heptane, or ethylene, or can be mixed with nitrogen, carbon monoxide, carbon dioxide and/or water vapor. Especially preferred is the use of natural gas, which can contain, for example, 80 to 98% methane by volume, plus small amounts of ethane—e.g., up to 7% by volume—and higher hydrocarbons, e.g., up to 3% by volume—as well as nitrogen, carbon dioxide and water vapor. Coke oven gas, petroleum gas or marsh gas can also be used as starting material, after having been freed of undesired accompanying substances such as hydrogen sulfide, hydrogen and/or relatively large amounts of hydrocarbons having a relatively great molecular weight. When other hydrocarbons, such as ethane for example, are used in the process of the invention in addition to methane, they, too, are transformed to formaldehyde, carbon oxides and water (cf. Example 11).

The oxygen can also be fed into the process in pure form or in mixture with other gases, such as nitrogen, carbon monoxide, carbon dioxide, noble gases, water vapor and/or hydrocarbons. Air is preferred as the oxygen-containing gas.

The amount of oxygen which is to be used in the process of the invention for the oxidation of methane to formaldehyde can vary within wide limits. For example, 0.01 to 100 moles of oxygen, reckoned as pure oxygen, can be used per mole of methane. Within this range, the explosion limits must, of course, be considered. Preferably from 0.05 to 20 moles of oxygen are used per mole of methane. The reactants, methane and oxygen, can of course be used in mixture with inert gases. Oxygen-methane mixtures can be used with a content of up to 98% by volume, e.g., up to 80% by volume, of inert gases. Thus, for example, the process of the invention can be performed in the presence of inert gases such as nitrogen, carbon monoxide, carbon dioxide and/or water vapor.

Especially preferred in the preparation of formaldehyde is the use of air and natural gas. Such a process is economically attractive. The volumetric ratio of air to natural gas is to be adjusted such as to remain within the abovespecified oxygen-methane limits. It is desirable to operate either with an excess of natural gas and a limited amount of air, or with a limited amount of natural gas and an excess of air; for example, 2 parts by volume of natural gas and 1 part of air, or one part of natural gas and 3 parts of air can be fed into the reaction.

Corresponding to the various possibilities of arranging the catalyst, the reactor may be constructed in various ways. If a fixed bed catalyst is used, the catalyst can be fixedly disposed, for example, in one or more reaction tubes (tubular reactor). The reaction tubes may be of metal, a ceramic composition, or quartz. Preference is given to metal tubes lined with a ceramic composition. If the catalyst is used in the form of a fluid bed, it is best to use a fluid bed reactor of conventional construction.

The feeding of the starting products to the reactor and the heating thereof can be performed in varous ways. For example, methane or methane-containing gases and oxygen or oxygen-containing gases can be mixed in a pressure chamber or in a mixing nozzle, and the starting mixture thus obtained can be preheated in the heat exchanger to 400° to 600° C, for example, and then be fed to the reactor where it will be further heated, if desired, to the reaction temperature. However, the heating of the reactants may also be performed separately and they can be fed separately to the reactor.

The rate of flow of the gas mixture in the reactor can vary within wide limits. For example, the rate of flow is so regulated as to result in contact times in the reaction chamber of 0.01 to 50 seconds, preferably from 0.05 to 5 seconds, reckoned for the amount of catalyst at a given reaction temperature.

The gases leaving the reactor contain unreacted starting products, including any inert gases that may have been added, as well as the reaction products, formaldehyde and water. The principal by-product that is formed is carbon monoxide, which may be accompanied by a small amount of carbon dioxide and formic acid. Other by-products may be methanol and acetaldehyde, but they are observed in no more than traces.

The reaction mixture leaving the reactor is generally subjected to further processing in a conventional manner. For example, the products can be separated in a washer, or by indirect cooling, or also be fractional cooling. For example, the washing can be performed with water, in which case a multi-stage washer can be used. An aqueous formaldehyde solution is obtained in this manner. From this solution commercial formaldehyde solutions can be prepared by distillation for immediate technical use. If the processing is performed by cooling, ice water, for example, can be used as the coolant; in this method of procedure the formaldehyde is condensed out of the reaction gas together with the water that has formed; in this manner, concentrated formaldehyde solutions in common commercial form can be obtained.

For the achievement of a high selectivity it may be desirable to conduct the reaction such that only a partial reaction will take place in a single pass through the reactor. For example, the pressure, temperature, composition of the starting gas mixture, the amount of catalyst and/or the rate of flow can be varied to bring this about. The gas remaining after separation of the formaldehyde can be recycled into the reactor. It is desirable to add to this gas the amounts of methane and oxygen that have been consumed, adding them in the form of natural gas and air, for example. In this manner a continuous circulation can be achieved. If the gas is recirculated in this manner, the inert gases and the by-products, especially carbon monoxide, will concentrate in the recycled gas, and any excessive accumulation of these gases can be prevented by a continuous or discontinuous side-stream removal. It is also desirable to replace the removed exhaust gas with an equal amount of fresh gas.

In a preferred embodiment of the process of the invention the following procedure is used. A fresh supply of natural gas and air is mixed in a blower with the recycled gas in a volumetric ratio of about 2 : 1, this fresh gas replacing the consumed amounts of methane and oxygen as well as the amount of the exhaust gas. The gas mixture produced in this manner is preheatd to about 400° to 600° C in a heat exchanger heated by the gases leaving the reactor, and is then fed into the reactor. In the reactor, the gas mixture is further heated to a reaction temperature of, say, 520° to 670° C. The reactor contains a fixedly disposed catalyst consisting of pure silicon dioxide having an internal surface area ranging from 80 to 250 m²/g BET, in the form of balls of a diameter of 0.4 to 4 mm. The reaction is performed at a pressure between 1 and 30 atmospheres. The rate of flow is adjusted so as to produce contact times ranging from 0.05 to 5 seconds. The gas mixture emerging from the reactor is first passed through the heat exchanger and then into a washer in which the formaldehyde is washed out with water. The aqueous formaldehyde solution is concentrated by distillation, to produce a conventional commercial formaldehyde solution. A portion of the gas mixture freed of formaldehyde is removed as exhaust gas and the remainder is recycled.

The process of the invention is distinguished from known processes by the fact that formaldehyde can be produced in large amounts in a simple manner, continuously, from cheap and easily available raw materials, with a high selectivity and yield. For example, 550 grams of formaldehyde can be obtained from one Nm³ of methane. The practice of the method of the invention is relatively simple, since all of the parameters of the reaction are variable within wide limits. None of the streams of gas and liquid occurring in the process is corrosive, so that there is no problem with regard to the material of the piping and containers. A special advantage of the method of the invention over other methods is that an exhaust gas is produced which contains methane and carbon monoxide. This exhaust gas can be used, for example, for further chemical reactions or, in view of its high heat value, for the recovery of energy. For example, the exhaust gas in the process of the invention can be used for preheating the input products and for raising the temperature of the reactor to the reaction temperature. In a system of suitable size, electrical power can be obtained in a power plant from the exhaust gas, with the admixture, if desired, of fresh natural gas. The economy of the process of the invention is enhanced, not impaired, by the exhaust gas that must be removed.

Formaldehyde is an important basic raw material for the chemical industry. Large amounts of formaldehyde are used in the production of resins, such as phenol-formaldehyde resins for example. In the form of aqueous solutions, formaldehyde can also be used as a reducing agent, a disinfectant, or as a preservative. For additional uses of formaldehyde, see Ullmann, supra, p. 670.

The invention will be further described in the following illustrative examples wherein all parts are by weight unless otherwise expressed.

EXAMPLE 1

An electrically heated quartz reaction tube 70 cm long and 1.78 cm in diameter was charged with 40 cm³ of a silicon dioxide catalyst consisting of grains of pure $SiO_2$ of spherical shape having an attrition-resistant surface and a specific surface area of 110 m²/g, the grain size distribution ranging from 0.4 to 2 mm diameter. The length of the catalyst section of the tube was 16 cm; the temperature in this section was maintained at a uniform 610° C, and the reaction took place therein.

In a mixing chamber having a volume of 1000 cm³, 35.8 l/h of air and 85.7 l/h of methane were fed and mixed at 25° C. The methane had a purity of 99.95% by volume. The starting gas composition was thus 29.5% air and 70.5% methane by volume, or 6.18% oxygen, 23.32% nitrogen and 70.5% methane by volume. The gas mixture thus obtained was heated in a preheater to 450° C and fed through the catalyst at 610° C and at a positive pressure of 30 cm $H_2O$. From the above data it was reckoned that the rate of throughput was 121.5 l/h, the velocity of flow was 42.4 cm/sec, and the contact time was 0.38 sec. The emerging reaction gas was passed through three plate-type washing flasks each containing 100 cm³ of water, for the purpose of determining the amount of formaldehyde that had formed. The quantitative analysis of the solution was performed both by gas chromatography and by titration. A Porapak-N column was used for the gas chromatographic analysis. The titrimetric determination of the formaldehyde was performed by the sulfite method.

After a reaction time of 6 hours, 8.49 g of formaldehyde were obtained, plus traces of methanol and formic acid as by-products. The gas mixture freed of formaldehyde was also analyzed by gas chromatography to determine the transformation and the CO and $CO_2$ content, using a Porapak-Q column and a 13X molecular sieve column. Under the conditions described, 3.2 vol. % of $O_2$ and 2.45 vol. % of methane had reacted, giving a transformation of 51.8% with respect to the oxygen input and 3.47% with respect to the methane input. The selectivity came to 29.1% with respect to $O_2$ and 38.1% with respect to $CH_4$, i.e., 38.1% of the reacted methane had been oxidized to formaldehyde. Virtually all of the balance was obtained as carbon monoxide. Carbon dioxide could be found only in small amounts, less than 0.1 vol. %. A carbon balance was established for the consumed methane (2.45 vol. %) and the formaldehyde and carbon monoxide formed (0.93 vol. % HCHO and 1.51 vol. % CO, respectively).

EXAMPLE 2

The same apparatus was used as in Example 1, but the gas mixture was composed of 29.7 vol. % air and 70.3 vol. % natural gas. The natural gas contained 86.53 col. % methane, 0.87 vol. % ethane, 0.14 vol. % higher hydrocarbons, 0.9 vol. % $CO_2$ and 11.56 vol. % nitrogen.

The gas mixture was passed at 605° C, at the rate of 181 l/h, through the same catalyst as in Example 1. After 30 hours of reaction time, 37.56 g of formaldehyde was obtained in the aqueous solution (determined by titration). The solution was tested by gas chromatography and thinlayer chromatography (as 2,4-dinitrophenylhydrazone) for higher aldehydes, alcohols, acids and ketones. These tests showed that the formeldehyde solution thus obtained had a high degree of purity. Aside from the usual by-products of formaldehyde in extremely small amounts (such as $CH_3OH$ (0.04 wt %) and HCOOH (0.26 wt %), no other products could be detected. The acetaldehyde concentration was less than 0.01%. Under these reaction conditions, 2.4 vol. % of oxygen and 1.8 vol. % of methane had reacted. The reaction gas contained 1.14 vol. % carbon monoxide and about 0.1 vol. % carbon dioxide. The transformation amounted to 38.4% with respect to the oxygen input and 2.96% with respect to the methane input. A selectivity was obtained of 31.2% with respect to reacted $CH_4$ and 23.1% with respect to $O_2$. This corresponded to a yield of 416 g HCHO per $Nm^3$ of $CH_4$.

EXAMPLE 3

A gas mixture of 4.7 vol. % oxygen and 95.3 vol. % methane was passed through 30 $cm^3$ of the same catalyst as described in Example 1, at a throughput rate of 93.6 l/h at 610° C.

The reaction gas was passed through a cooling trap located in an ice-water vessel, and then through a gas washing flask. After a reaction time of 21 hours, 41.2 g of 26.5% aqueous formaldehyde solution was obtained in the cooling trap. The solution also contained 0.17% formic acid and traces of methanol. In all, 14.8 g of formaldehyde was obtained. The oxygen transformation was 49%. The selectivity was 26% with respect to oxygen and 34.3% with respect to methane. The gas mixture leaving the reaction contained 1.07 vol. % of carbon monoxide.

EXAMPLE 4

The procedure was the same as in Example 2, but 40 $cm^3$ of pure silicon dioxide with a specific surface area of 217 $m^2/g$ was used as catalyst, which was in the form of sausage-shaped pellets 4 to 10 mm long and 2 to 3 mm in diameter. The reaction temperature was 640° C. The gas mixture consisted of 30.6 vol. % air and 69.4 vol. % natural gas with the composition as described in Example 2. The throughput rate amounted to 214 l/h and the contact time 0.22 sec. After 5 hours of reaction time under these conditions, 4.4 g of formaldehyde was obtained. The transformation was 22.1% with respect to the oxygen input. In addition, 0.6 vol. % CO and 0.07 vol. % $CO_2$ had formed. The selectivity amounted to 23.4% with respect to oxygen, and 31.3% with respect to methane.

EXAMPLE 5

A gas mixture of 5.7 vol. % methane and 94.3 vol. % oxygen was passed at 645° C through 40 $cm^3$ of the same catalyst as in Example 1 at a throughput rate of 79 l/h. The contact time was 0.58 sec. The transformation with respect to methane input was 28.9%. After 5 hours of operating time, 1.55 g of formaldehyde was obtained. The selectivity was 19.1% with respect to methane.

EXAMPLE 6

The procedure was the same as in Example 2, but the air and natural gas mixture was passed at 620° C through a catalyst consisting of 87% $SiO_2$, 2.5% CaO, 6.5% $Al_2O_3$, 1% MgO, 1% $Na_2O$, and 2% $H_2O$, at a throughput rate of 128.5 l/h. The specific surface area and the grain size distribution of the catalyst were 90 $m^2/g$ and 0.4 to 2 mm, respectively. After 6 hours of reaction time, 5.33 g of formaldehyde was obtained. 2.3 vol. % of oxygen and 1.71 vol. % of methane had been reacted. The selectivities were thus 24.1% with respect to oxygen and 32.2% with respect to methane.

EXAMPLE 7

The procedure was the same as in Example 6, except that a catalyst was used which was composed of 1% $Al_2O_3$, 2% $H_2O$ and 97% $SiO_2$. The specific surface area was 185 $m^2/g$. The grain size ranged from 2 to 5 mm. At 612° C the transformation was 26.7% with respect to oxygen. The CO concentration in the reaction gas was 0.86 vol. %. After 6 hours 3.37 g of formaldehyde had been obtained. The selectivity was thus 29.1% with respect to methane.

EXAMPLE 8

The procedure was the same as in Example 1, but water was added to the air-methane gas mixture. The composition of the gas mixture 29.5 vol. % air, 2.8 vol. % water and 67.7 vol. % methane, and the throughput was 127 l/h. At 610° C, after 4 hours of reaction time, 4.1 g of formaldehyde had been obtained. The reaction gas contained 0.91 vol. % CO. 2vol. % $O_2$ and 1.55 vol. % $CH_4$ had reacted. The selectivity was thus 32.3% with respect to $O_2$ and 41.7% with respect to $CH_4$. This corresponded to a yield of 558 g of formaldehyde per cubic meter of methane at normal temperature and pressure.

EXAMPLE 9

The procedure was the same as in Example 2, but carbon monoxide was added to the air-natural gas mixture which was fed through the catalyst at 608° C with the following composition: 28.2 vol. % air, 4.2 vol. % carbon monoxide and 67.6 vol. % natural gas, at a throughput of 208 l/h. After 4.5 hours, 6.19 g of formaldehyde was found. The transformation was 40.6% with respect to oxygen and 3.03% with respect to methane. The selectivity was thus 22.1% with respect to oxygen and 29.8% with respect to methane.

EXAMPLE 10

In a micro-pressure apparatus having a reaction chamber lined with quartz, 8.6 $cm^3$ of the same catalyst as described in Example 1 was installed. The depth of the catalyst charge was 3.44 cm, and its cross sectional area was 2.5 $cm^2$. Through this catalyst charge was passed a gas mixture of 27.6 vol. % air and 72.4 vol. % natural gas at an excess pressure of 5 atm, and at a temperature of 570° C. The throughput rate of the gas mixture was 283 l/h. After 3.5 hours of reaction time, 4.5 g of formaldehyde was determined by titration. The CO concentration in the reaction gas was 0.95 vol. %. 1.8 vol. % oxygen and 1.32 vol. % methane had reacted. The selectivity thus came to 20.3% with respect to oxygen and 27.6% with respect to methane. The volume-time yield of formaldehyde under these reaction conditions amounted to 150 g/l/h. This example shows that higher yields are obtained at elevated pressures.

EXAMPLE 11

The procedure was the same as in Example 1, but a gas mixture of 34.7 vol. % air and 65.3 vol. % ethane was fed through the catalyst section at a rate of 172.2 l/h at 558° C. The ethane had a purity of 99.95%. 0.3 vol. % CO and 0.06 vol. % $CO_2$ were found in the reaction gas. The transformation with respect to oxygen was 17.8%. After 5 hours of reaction time, 2.89 g of formaldehyde was found in the aqueous solution. The foregoing example shows that ethane is also converted to formaldehyde. Accordingly, both components of natural gases containing various amounts of methane and ethane will be converted to formaldehyde.

It will be appreciated that the instant specification and examples are set forth by way of illustration and not limitation, and that various modifications and changes may be made without departing from the spirit and scope of the present invention.

What is claimed is:

1. In the gas phase reaction of methane and oxygen at elevated temperature to form formaldehyde, the improvement which comprises effecting the reaction at a temperature of about 450° to 750° C and a pressure of about 1 to 100 atmospheres in the presence of silicon dioxide as catalyst, the silicon dioxide having an internal surface area of about 30 $m^2/g$ to 500 $m^2/g$, the silicon dioxide being unmixed or mixed with at least one other oxide selected from the group consisting of oxides of aluminum, iron, vanadium, molybdenum, tungsten, calcium, magnesium, sodium and potassium.

2. The process of claim 1, wherein the oxygen is introduced as air.

3. The process of claim 1, wherein the contact time between oxygen and methane is about 0.01 to 50 seconds.

4. The process of claim 3, wherein the silicon dioxide is mixed with at least one other oxide, such other oxide being present in about 5 to 50% by weight of the mixture, the catalyst has an internal surface area of about 50 to 500 $m^2/g$, the temperature is about 520° to 670° C and the pressure is about 1 to 30 atmospheres, the oxygen is introduced as air and is present in about 0.01 to 100 times the molar amount of the methane which is introduced as natural gas.

* * * * *